United States Patent [19]

Bergman

[11] 4,214,581
[45] Jul. 29, 1980

[54] FOLDABLE FIRST-AID DRESSINGS WITH EQUAL BANDAGE AND COMPRESS WIDTHS

[76] Inventor: Bertil N. Bergman, Skogsgränd 10, S-952 00 Kalix, Sweden

[21] Appl. No.: 909,856

[22] Filed: May 26, 1978

[30] Foreign Application Priority Data

Jun. 15, 1977 [SE] Sweden ............................... 7706963

[51] Int. Cl.² .............................................. A61F 13/00
[52] U.S. Cl. .................................... 128/155; 128/157
[58] Field of Search ............... 128/155, 156, 166, 284, 128/287, 284, 169, 170, 168, 325, 296, 132 D; 270/39, 40, 69, 79

[56] References Cited

U.S. PATENT DOCUMENTS

| 703,627 | 7/1902 | Utermöhlen | 128/156 |
|---|---|---|---|
| 1,705,366 | 3/1929 | Johnson | 128/296 UX |
| 2,321,363 | 6/1943 | Crowley | 128/156 |
| 3,029,816 | 4/1962 | Neils | 128/284 |
| 3,120,229 | 2/1964 | Hinkamp | 128/169 |

FOREIGN PATENT DOCUMENTS

| 603186 | 4/1926 | France | 128/170 |
|---|---|---|---|
| 2226188 | 11/1974 | France | 128/325 |
| 255250 | 6/1948 | Switzerland | 128/155 |

OTHER PUBLICATIONS

"First Aid Textbook" American Red Cross Doubleday & Co. Inc. Garden City, NY Fourth Edition, May, 1965 pp. 190–197.

Primary Examiner—William E. Kamm
Assistant Examiner—J. Kruter
Attorney, Agent, or Firm—Sughrue, Rothwell, Mion, Zinn and Macpeak

[57] ABSTRACT

A first-aid dressing comprising a bandage and a compress arranged thereon. Both the bandage and the compress are folded at least double in the longitudinal direction of the bandage, which is elastically stretchable in the longitudinal direction thereof. The compress is so formed and so applied to the bandage that when the bandage is unfolded to twice its width the compress can be unfolded to a width which, even in this state of the bandage, coincides substantially with the width of the bandage.

6 Claims, 6 Drawing Figures

FOLDABLE FIRST-AID DRESSINGS WITH EQUAL BANDAGE AND COMPRESS WIDTHS

The present invention relates to a dressing, and more particularly, although not exclusively, to a dressing which can be readily used as a first-aid dressing.

Those dressings mostly used today in first-aid comprise a relatively narrow bandage and a compress which is placed generally centrally of the two ends of the bandage and which is considerably wider than said bandage. A serious disadvantage with such a dressing is that the bandage is quite inflexible, which means, inter alia, that when the dressing is used as a pressure-dressing, there is a grave risk of the blood vessels being strangulated. This risk is enhanced by the fact that the narrow and thin bandage of said dressing readily becames twisted. Moreover, because the bandage is much narrower than the compress, it is difficult to hold the whole of the compress tightly in place over a large wound or sore. The bandage is also relatively weak.

In addition to the difficulty of holding the whole of the compress of the known dressing comprising a narrow bandage effectively over a large wound or sore, is the difficulty of holding the compress in place on certain parts of the body. Furthermore, because in their packeted condition the bandages of the known dressings are rolled-up from each end with the rolls laid on the compress, it is difficult to apply the dressing to the wound quickly; in addition to which the bandage and compress are liable to become dirty as the bandage is unwound. Moreover, the known dressing cannot be adapted to suit wounds of different sizes.

The main object of the present invention is to provide a sterile dressing in which the aforementioned disadvantages are eliminated. This object is achieved by the fact that both the bandage and the compress are folded at least double in the longitudinal direction of the bandage; that the bandage is elastically stretchable in the longitudinal direction thereof; and that the compress is so formed and so applied to the bandage that when unfolding the bandage to its double width the compress can be unfolded to obtain a width which, even in this state of the bandage, coincides substantially with the width of the bandage.

In a preferred embodiment, the bandage comprises a triangular piece of fabric or cloth which in the narrowest state of the dressing is double-folded at least three times on fold lines extending parallel with one of the edges of said piece of fabric or cloth. The fabric or cloth conveniently has the shape of an isosceles triangle and is folded on lines extending parallel with the base of the triangle. To obtain a bandage stretchable in the longitudinal direction, the fabric or cloth is suitably folded on lines which form angles with the directions of the threads in said fabric, i.e. the fabric is cut on the bias.

By forming the compress such that in the narrowest state of the dressing the compress is double-folded twice along fold lines extending parallel with the fold lines of the cloth, the folded dressing can be unfolded to form a dressing whose width is four times that of the narrowest dressing. In order to allow the compress to be unfolded also in the longitudinal direction, it may first be double folded along fold lines extending perpendicularly to the fold lines of the cloth. As a result of the design imparted to the cloth, the dressing, even in this state, can be quickly and readily applied to different parts of the body, said dressing being intended to cover large sores and wounds, such as burns.

In order to enable the dressing to be readily unpacked whilst keeping the dressing clean, the bandage, in the packed state of the dressing, is conveniently folded in over the compress from both ends of the bandage in a manner such that said ends can be readily reached and such that the dressing can be easily made for use by pulling the two ends of the bandage in the longitudinal direction thereof.

Exemplary embodiments of the invention will now be described with reference to the accompanying schematic drawing, in which.

Figure 1:
FIG. 1 illustrates a first embodiment of a dressing in its narrowest state.
Figure 2:
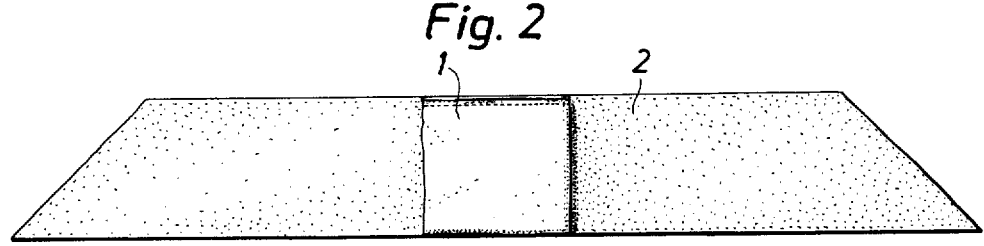
FIG. 2 illustrates the dressing shown in FIG. 1 in an unfolded state.

The dressing illustrated in FIG. 1 comprises a compress 1 and a bandage 2. The bandage is double-folded at least once in the region of the compress, which is also double-folded. This means that in addition to having the width illustrated in FIG. 1, the dressing can also be unfolded to obtain a width twice that of the FIG. 1 dressing, as illustrated in FIG. 2. In both cases the bandage 1 covers the whole width of the compress, which means that the compress can be pressed more effectively against a sore or wound. The width of the bandage also causes the force with which the bandage is tightened to be distributed over a wide area, and hence the pressure becomes relatively low. When the bandage 2 is made from an elastically stretchable textile material, it can be tightened extremely hard, e.g. when applying a pressure-dressing, without danger of strangulating blood vessels. Blood pulsations are able to propagate as a result of the resiliency of the bandage 2.

Figure 3:
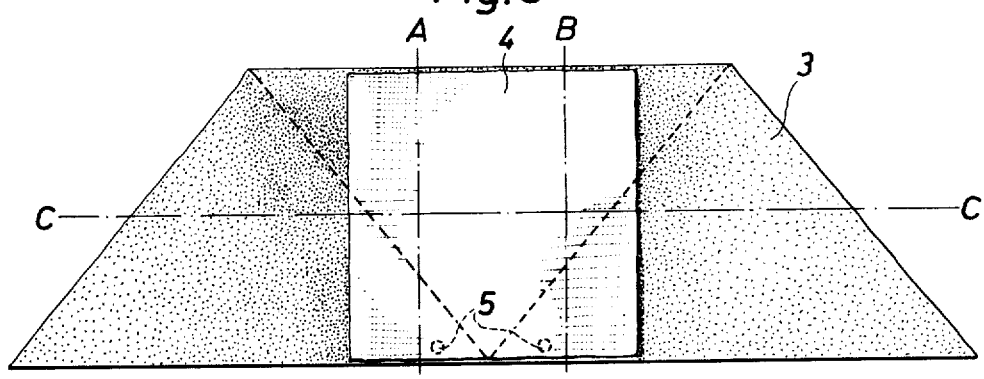
FIGS. 3-5 illustrate a second embodiment of a dressing with three different folding widths.

Although not evident from FIGS. 1 and 2, the bandage 2 is preferably obtained by folding a piece of triangular cloth, as shown in FIG. 3, said triangle suitably being an isosceles triangle with the base coinciding with one longitudinal edge of the bandage. Thus, the width illustrated in FIG. 1 can, for example, correspond to folding said cloth three times, which means that the bandage 2 of the FIG. 1 embodiment comprises eight layers in the region of the compress 1. The number of layers of the FIG. 2 embodiment is four.

Figure 4:
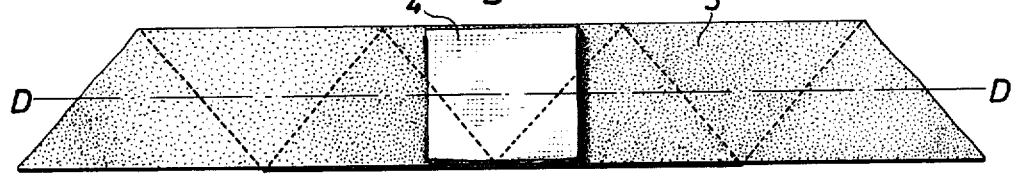
Figure 5:

In FIGS. 3-5 there is illustrated a dressing according to the invention whose bandage comprises a triangular piece of cloth. FIG. 3 illustrates the bandage in its widest state, the apex of the cloth 3 being folded down to the base. The bandage is provided with a compress 4 which in the illustrated state of the dressing covers the whole width of the cloth 3 and which is detachably bonded to said cloth at two points 5. The apex of the cloth may be folded down on the rear side of the cloth, as illustrated, or between the compress and the cloth. A dressing of this width is particularly intended for use in the case of large sores or wounds, such as burns, and can readily be applied to different parts of the body with uniform abutment of the compress thereagainst.

For the purpose of providing a narrower dressing, the dressing shown in FIG. 3 is intended to be folded on fold lines A—A, B—B, and C—C. In this case, the compress 4 is first folded in towards the middle on fold lines A—A and B—B, respectively, and then forwards on the line C—C. The cloth 3 is also folded rearwardly on the fold line C—C. The resultant dressing, whose width corresponds to half the width of the dressing shown in FIG. 3, is illustrated in FIG. 4. In principle this dressing coincides with the dressing illustrated in FIG. 2.

By folding the compress 4 once more in the forward direction on a fold line D—D and the cloth 3 rearwardly on the same fold line, there is obtained a dressing such as that illustrated in FIG. 5, this dressing corresponding in width to the dressing shown in FIG. 1. This width of the dressing is that which the dressing has when packed and is the width most used, a dressing of this width being particularly suitable, inter alia, as a pressure dressing. The cloth is therewith double-folded three times in the region of the compress 4, i.e. it forms eight layers.

The wide bandage 2, which is multi-layered in the region of the compress 1 and which has tapering single end portions, can be applied rapidly and simply in all cases to provide an effective dressing without risk of those strangulating effects liable with previously known first-aid dressings where the relatively narrow and thin bandage readily becomes twisted to exert substantially the same local pressure as that obtained when tightening a narrow belt or rope. Tests have shown, for example, that a person not educated in the arts of the nursing profession can effectively apply a pressure dressing when using a dressing according to the invention in a time of less than 30 seconds whilst the application of a corresponding dressing using first-aid dressings of types known today may take more than three minutes. The essential characteristics of the dressing are that it can be unfolded to different widths; that the compress in all cases, has a width which coincides substantially with the width of the bandage; that the compress, in all cases, can be applied with a uniformly distributed pressure; and that the dressing can be readily applied in all states.

Figure 6:
FIG. 6 illustrates how the bandage is folded in the packed condition of the dressing.

A further important characteristic of a first-aid dressing is that it shall be absolutely sterile. The aforementioned, known first-aid dressing is packed with the bandage rolled up from both ends thereof and with the rolls of bandage placed on the compress in a sterile plastic casing. In addition to it being realtively troublesome to unroll the rolled parts of the bandage, there is also a danger of the compress becoming soiled as a result of the fingers of the user coming into contact therewith. To overcome this, the dressing according to the invention is packed with the ends of the bandage folded inwardly over and protecting the compress in a manner such that the ends of the bandage are placed uppermost and are readily reached by the user, as illustrated schematically in FIG. 6 which is a cross-sectional view of a dressing in its packed state. Thus, the user need only grip the two ends of the bandage placed uppermost on the packed dressing and pull them outwardly in the longitudinal direction of the bandage in order to extend the dressing. Thus, there is no risk of touching the compress. Moreover, the dressing can be prepared ready for use much more quickly than a dressing in which the rolls need to be unwound; furthermore, the rolled bandage tends to twist when unrolling said ends, which is a further disadvantage of known dressings.

The elastic, stretchablility of the bandage of the dressing according to the invention is created, as mentioned above, by cutting the bandage from a piece of cloth on the bias, i.e. in a manner such that the directions of the threads in the material from which the bandage is made will form angles with the longitudinal direction of the bandage. These angles may be approximately 45°. In the case of a bandage formed from a triangular cloth of for instance the measurement 90×90×130 cm, it is possible, as a result of cutting the cloth on the bias, to obtain a stretchability corresponding to an extension of the bandage of approximately 30 cm with maximum stretching.

As will be understood, the shape, the size and the number of layers contained by the bandage and compress can be varied as desired and as necessary. The illustrated embodiment, however, is particularly well suited as a protective dressing or pressure-dressing and also as a support dressing. Of course, the triangular cloth may be obtained by folding a rectangular cloth diagonally.

By way of summary it can be said that a first-aid dressing according to the invention has the following essential characteristics. It:

(a) is of simple design;

(b) can be readily applied by a person not trained in first-aid;

(c) is very effective with all types of external wounds and sometimes also in the case of internal bleeding;

(d) can be rapidly applied to all types of wounds and sores;

(e) can be adapted to suit sores and wounds of different sizes;

(f) is the only readily-packed, sterile dressing which can be used readily, safely and effectively to stem bleeding of the carotid artery and the inguinal artery;

(g) is a dressing which can be used with good results as a support bandage; and (h) is a dressing which can often be readily applied by the injured person himself.

What I claim is:

1. A first-aid medical dressing, comprising:
   (a) a bandage member having two laterally opposite, parallel, longitudinally oriented edges, and being elastically stretchable in the longitudinal direction,
   (b) a rectangular compress centrally arranged on said bandage member with opposite ones of its edges aligned with the laterally opposite edges of the bandage member, and being attached thereto along one of said aligned edges,
   (c) the compress being folded over itself in the longitudinal direction of the bandage member to at least a double thickness by a fold in a first direction, and
   (d) the bandage member being folded under itself in the longitudinal direction thereof to at least a double thickness in a central area thereof coextensive with said compress by a fold in a second, opposite direction,
   (e) whereby the bandage member and compress may be unfolded to twice their widths with the compress still extending across the full width of the bandage member.

2. A dressing according to claim 1, wherein the bandage member comprises a substantially triangular cloth which, in the narrowest state of the dressing, is double-folded at least three times along fold lines extending parallel with one edge of the cloth.

3. A dressing according to claim 2, wherein the cloth has the form of an isosceles triangle and is folded about lines extending parallel with the base of the triangle.

4. A dressing according to claim 2, wherein the compress in the narrowest state of the dressing is double-folded twice along fold lines extending parallel with the fold lines of the cloth.

5. A dressing according to claim 4, wherein the compress is first double-folded along fold lines extending perpendicularly to the fold lines of the cloth.

6. A dressing according to claim 1 packed in its narrowest state, wherein the bandage member is folded in over the compress from both ends of the bandage member in a manner such that said ends lie on the exterior of the packed dressing to enable the bandage member to be readily extended by pulling the two ends thereof in the longitudinal direction.

* * * * *